United States Patent
Truschel et al.

(10) Patent No.: US 9,717,868 B2
(45) Date of Patent: Aug. 1, 2017

(54) OBESITY HYPVENTILATION SYNDROME TREATMENT SYSTEM AND METHOD

(75) Inventors: William A. Truschel, Eindhoven (NL); Christopher Anthony Procyk, Eindhoven (NL); Mark Christopher McDermott, Eindhoven (NL); Anandi Mahadevan, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 304 days.

(21) Appl. No.: 13/885,877

(22) PCT Filed: Nov. 15, 2011

(86) PCT No.: PCT/IB2011/055089
§ 371 (c)(1),
(2), (4) Date: May 16, 2013

(87) PCT Pub. No.: WO2012/069957
PCT Pub. Date: May 31, 2012

(65) Prior Publication Data
US 2013/0247914 A1 Sep. 26, 2013

Related U.S. Application Data
(60) Provisional application No. 61/416,336, filed on Nov. 23, 2010.

(51) Int. Cl.
*A61M 16/00* (2006.01)
*A61M 16/16* (2006.01)
*A61M 16/10* (2006.01)

(52) U.S. Cl.
CPC ........ *A61M 16/00* (2013.01); *A61M 16/0051* (2013.01); *A61M 16/0069* (2014.02);
(Continued)

(58) Field of Classification Search
None
See application file for complete search history.

(56) References Cited

U.S. PATENT DOCUMENTS

| | | | |
|---|---|---|---|
| 5,129,390 A * | 7/1992 | Chopin | A61M 16/00 128/204.21 |
| 6,105,575 A | 8/2000 | Estes | |

(Continued)

FOREIGN PATENT DOCUMENTS

| | | |
|---|---|---|
| JP | 2002315831 A | 10/2002 |
| JP | 2009524456 A | 7/2009 |

(Continued)

OTHER PUBLICATIONS

Capucine et al., "Simplified Method to Measure Respiratory-Related Changes in Arterial Pulse Pressure in Patients Receiving Mechanical Ventilation", Chest, Aug. 2003, 124, 2, pp. 665-670.

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

A pressurized flow of breathable gas is delivered to the airway of a subject in accordance with a therapy regimen. The therapy regimen calls for maintenance of an average tidal volume. The therapy ensures that the subject breaths at a therapeutic breath rate. The breath rate may be determined dynamically based on breathing of the subject early on in a therapy session and/or based on a detected wakefulness of the subject. Inspiration for spontaneous and non-spontaneous breaths may be supported at different levels. The therapy regimen further maintains a beneficial positive end expiratory pressure, to reduce respiratory obstructions and/or for other purposes.

21 Claims, 4 Drawing Sheets

(52) U.S. Cl.
CPC ... *A61M 16/161* (2014.02); *A61M 2016/0021* (2013.01); *A61M 2016/0027* (2013.01); *A61M 2016/0039* (2013.01); *A61M 2016/102* (2013.01); *A61M 2205/3365* (2013.01); *A61M 2205/3368* (2013.01); *A61M 2205/3375* (2013.01); *A61M 2205/502* (2013.01); *A61M 2205/505* (2013.01); *A61M 2230/40* (2013.01); *A61M 2230/43* (2013.01); *A61M 2230/60* (2013.01); *A61M 2230/62* (2013.01); *A61M 2230/63* (2013.01)

(56) References Cited

U.S. PATENT DOCUMENTS

| | | | |
|---|---|---|---|
| 7,094,206 B2 * | 8/2006 | Hoffman | A61B 5/0809 600/529 |
| 7,267,122 B2 | 9/2007 | Hill | |
| 2001/0027792 A1 * | 10/2001 | Berthon-Jones | A61M 16/00 128/204.23 |
| 2003/0066528 A1 * | 4/2003 | Hill | A61M 16/00 128/204.18 |
| 2005/0109340 A1 | 5/2005 | Tehrani | |
| 2006/0070624 A1 * | 4/2006 | Kane | A61M 16/00 128/204.23 |
| 2008/0066753 A1 * | 3/2008 | Martin | A61M 16/0051 128/204.23 |
| 2008/0183239 A1 * | 7/2008 | Tehrani | A61N 1/36132 607/42 |
| 2008/0236582 A1 * | 10/2008 | Tehrani | A61H 31/02 128/204.22 |
| 2008/0302364 A1 * | 12/2008 | Garde | A61M 16/0045 128/204.23 |
| 2009/0024008 A1 * | 1/2009 | Brunner | A61M 16/0051 600/301 |
| 2010/0108066 A1 * | 5/2010 | Martin | A61M 16/0051 128/204.23 |
| 2010/0186743 A1 * | 7/2010 | Kane | A61M 16/00 128/204.23 |
| 2011/0017214 A1 * | 1/2011 | Tehrani | A61M 16/0051 128/204.22 |
| 2011/0240025 A1 * | 10/2011 | Mechlenburg | A61M 16/00 128/204.21 |
| 2012/0298108 A1 * | 11/2012 | Kane | A61M 16/0051 128/204.23 |
| 2013/0199532 A1 * | 8/2013 | Shissler | A61B 5/0826 128/204.23 |

FOREIGN PATENT DOCUMENTS

| | | |
|---|---|---|
| WO | WO9640337 A1 | 12/1996 |
| WO | WO9812965 A1 | 4/1998 |
| WO | WO0076389 A2 | 12/2000 |
| WO | WO2007085110 A1 | 8/2007 |
| WO | WO2010115166 A1 | 10/2010 |
| WO | WO2011017033 A2 | 2/2011 |

* cited by examiner

OBESITY HYPVENTILATION SYNDROME TREATMENT SYSTEM AND METHOD

CROSS-REFERENCE TO RELATED APPLICATIONS

This patent application claims the priority befit under 35 U.S.C. §371 of international patent application no. PCT/IB2011/055089, filed Nov. 15, 2011, which claims the priority benefit under 35 U.S.C. §119(e) of U.S. Provisional Application No. 61/416,336 filed on Nov. 23, 2010, the contents of which are herein incorporated by reference.

BACKGROUND OF THE INVENTION

1. Field of the Invention

The invention relates to the delivery of therapy to a subject to treat respiratory disorders in which average tidal volume, respiratory rate, and/or positive end expiratory pressure are controlled automatically.

2. Description of the Related Art

Obesity Hypoventilation Syndrome is a respiratory syndrome where obese subjects (e.g., subjects with >30 kg/m2 Body Mass Index) suffer from hypoxia and hypercapnia resulting from shallow or insufficient respiration. Other syndromes and/or conditions have these and/or other symptoms. Systems configured to deliver pressurized gas to the airway of such subjects to facilitate respiration are known. Such systems include systems that are configured to maintain a therapeutic respiratory rate and an average tidal volume per breath.

In conventional systems, the therapeutic respiratory rate may be a setting that is configured by a user (e.g., a subject, a caregiver, a therapy decision-maker, a researcher, and/or other users). In such systems, the therapeutic respiratory rate may not take into account measurements of spontaneous respiration by a subject.

Typically, in systems that maintain an average tidal volume, every breath is supported at the same pressure levels. These systems generally are not configured to support spontaneous and non-spontaneous breaths at different pressure levels.

SUMMARY OF THE INVENTION

Accordingly, it is an object of the present invention to provide a therapy system that overcomes the shortcomings of conventional systems. This object is achieved according to one embodiment of the present invention by providing a system configured to deliver a pressurized flow of breathable gas to the airway of a subject. In one embodiment, the system comprises a pressure generator, a sensor, and one or more processors. The pressure generator is configured to generate a pressurized flow of breathable gas for delivery to the airway of a subject. The sensor is configured to generate an output signal conveying information related to respiratory effort by the subject. The one or more processors are configured to execute computer program modules including a control module, an inspiration pressure module, a rate determination module, and an expiration pressure module. The control module is configured to control the pressure generator in accordance with a therapy regimen such that an average tidal volume is maintained during breaths for the subject, and such that the breaths occur at a respiratory rate. The inspiration pressure module is configured to determine an inspiratory pressure level that will maintain an average tidal volume. The rate determination module is configured to determine a therapeutic respiratory rate. The expiration pressure module is configured to determine an expiratory pressure level. The control module is further configured to control the pressure generator such that respiration by the subject is maintained at the therapeutic respiratory rate, and such that during inspirations the pressurized flow of breathable gas is delivered at the inspiratory pressure level determined by the inspiration pressure module, and during expirations the pressurized flow of breathable gas is delivered at the expiratory pressure level.

Another aspect of the this disclosure relates to a method of delivering a pressurized flow of breathable gas to the airway of a subject. In one embodiment, the method comprises generating a pressurized flow of breathable gas for delivery to the airway of a subject; generating an output signal conveying information related to respiratory effort by the subject; dynamically determining an inspiratory pressure level that will maintain an average tidal volume; dynamically determining an expiratory pressure level; dynamically determining a therapeutic respiratory rate; and controlling the generation of the pressurized flow of breathable gas in accordance with a therapy regimen such that breaths of the subject occur at the therapeutic respiratory rate, and such that during inspirations the pressurized flow of breathable gas is delivered at the inspiratory pressure level determined by the inspiration pressure module, and during expirations the pressurized flow of breathable gas is delivered at the expiratory pressure level.

Yet another aspect of the invention relates to a system configured to deliver a pressurized flow of breathable gas to the airway of a subject. In one embodiment, the system comprises means for generating a pressurized flow of breathable gas for delivery to the airway of a subject; means for generating an output signal conveying information related to respiratory effort by the subject; means for dynamically determining an inspiratory pressure level that will maintain an average tidal volume; means for dynamically determining an expiratory pressure level; means for dynamically determining a therapeutic respiratory rate; and means for controlling the generation of the pressurized flow of breathable gas in accordance with a therapy regimen such that breaths of the subject occur at the therapeutic respiratory rate, and such that during inspirations the pressurized flow of breathable gas is delivered at the inspiratory pressure level determined by the inspiration pressure module, and during expirations the pressurized flow of breathable gas is delivered at the expiratory pressure level.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
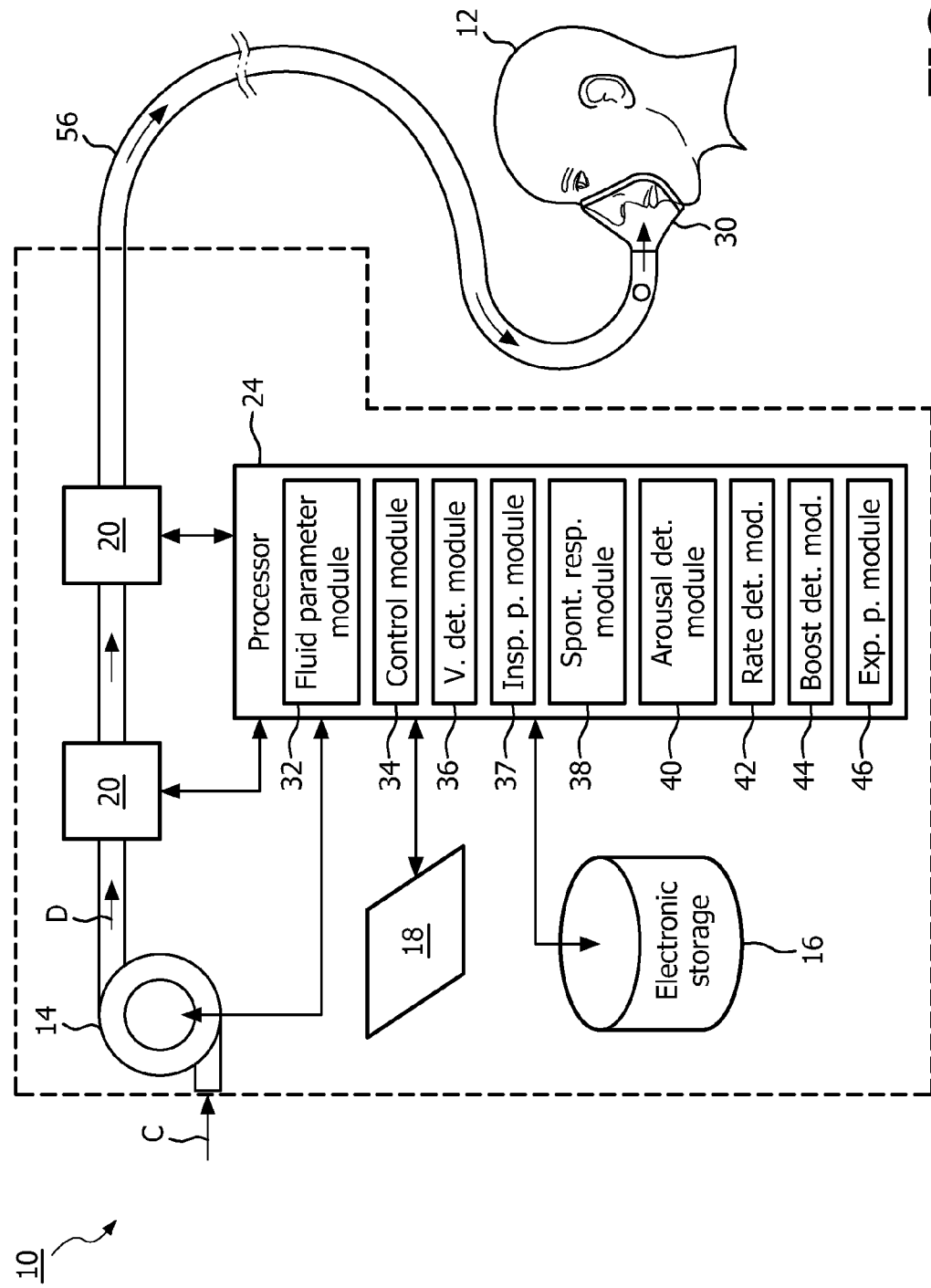
FIG. 1 illustrates a system configured to deliver a pressurized flow of breathable gas to the airway of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to deliver a pressurized flow of breathable gas to the airway of a subject 12 in accordance with a therapy regimen. The therapy regimen may be designed to treat a respiratory condition, such as Obesity Hypoventilation Syndrom (OHS), Obstructive Sleep Apnea (OSA), and/or other respiratory conditions. The therapy regimen calls for maintenance of an average tidal volume, maintenance of a respiratory rate, and/or maintenance of a positive end expiratory pressure. System 10 is configured to provide therapy to subject 12 as subject 12, to ensure that subject 12 breaths at a therapeutic respiratory rate. The respiratory rate may be determined dynamically based on breathing of subject 12 early on in a therapy session and/or based on a detected wakefulness of the subject. System 10 may be configured such that spontaneous breaths may be supported at a pressure that is lower than a pressure for breaths that are not spontaneous and are triggered automatically based on the therapeutic respiratory rate. In one embodiment, system 10 includes one or more of a pressure generator 14, electronic storage 16, a user interface 18, one or more sensors 20, a processor 24, and/or other components.

In one embodiment, pressure generator 14 is configured to generate a pressurized flow of breathable gas for delivery to the airway of subject 12. Pressure generator 14 may control one or more parameters of the pressurized flow of breathable gas (e.g., flow, pressure, volume, humidity, temperature, gas composition, etc.) for therapeutic purposes, or for other purposes. The one or more parameters may be controlled in accordance with a therapy regimen (e.g., as discussed further below). The therapy regimen may be configured to sustain and/or otherwise improve the quality of life in subject 12. By way of non-limiting example, pressure generator 14 may be configured to control the pressure of the pressurized flow of breathable gas in order to treat respiratory insufficiency or obstructed airway syndrome. The pressure generator may include a positive pressure generator configured to provide a positive airway pressure therapy to subject 12. Such a device is described, for example, in U.S. Pat. No. 6,105,575, hereby incorporated by reference in its entirety.

The pressurized flow of breathable gas is delivered to the airway of subject 12 via an interface 26. Interface 26 is configured to communicate the pressurized flow of breathable gas generated by pressure generator 14 to the airway of subject 12. As such, interface 26 includes a conduit 28 and an interface appliance 30. Conduit conveys the pressurized flow of breathable gas to interface appliance 30, and interface appliance 30 delivers the pressurized flow of breathable gas to the airway of subject 12. Some examples of interface appliance 30 may include, for example, an endotracheal tube, a nasal cannula, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

Although FIG. 1 illustrates the configuration of system 10 with interface 26 as being a single-limb, passive system, this is not intended to be limiting. It will be appreciated that the scope of this disclosure includes embodiments in which the interface 26 is formed as a two-limbed system including a second conduit configured to receive exhalation from interface appliance 30. The second conduit may exhaust such fluid to atmosphere, may convey such fluid to a filter, and/or convey such fluid to other components including a component within system 10.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 24, etc.).

User interface 18 is configured to provide an interface between system 10 and one or more users (e.g., subject 12, a caregiver, a researcher, a therapy decision-maker, etc.) through which the users may provide information to and receive information from system 10. This enables data, cues, results, and/or instructions and any other communicable items, collectively referred to as "information," to be communicated between the users and one or more of pressure generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14. User interface 18 may be configured to receive input from subject 12 to modify tunable parameters of system 10. For example, user interface 18 may be configured to receive input from subject 12 to modify or select sensitivity or response time of the respiratory state detection (e.g., the threshold level for breathing state transition detection may be adjusted for either an increase or a decrease in sensitivity with a graduated knob or a digital interface displaying a number from 1 to 10).

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

Sensors 20 are configured to generate one or more output signals conveying information related to respiratory effort of subject 12. In one embodiment, sensors 20 generate output signals conveying information related to one or more fluid parameters of the pressurized flow of breathable gas. The one or more parameters may include, for example, one or more of a flow, a volume, a pressure, a composition (e.g., concentration(s) of one or more constituents), humidity, temperature, acceleration, velocity, acoustics, changes in a parameter indicative of respiration, and/or other fluid parameters. In one embodiment, sensors 20 are a flow sensor and a pressure sensor. The sensors may include one or more sensors that measure such parameters directly (e.g., through fluid communication with the pressurized flow of breathable gas at pressure generator 14 or in subject interface 26). Sensors 20 may include one or more sensors that generate output signals related to one or more fluid parameters of the pressurized flow of breathable gas indirectly. For example, one or more of sensors 20 may generate an output based on an operating parameter of pressure generator 14 (e.g., a valve driver or motor current, voltage, rotational velocity, and/or other operating parameters), and/or other sensors.

Other output signals conveying information related to respiratory effort are contemplated. For example, sensors 20 may include a sensor that mechanically detects respiratory muscle effort (e.g., worn on a band around the chest of subject 12), an optical sensor that captures images of subject 12 and/or measures the position and/or motion (e.g., velocity or acceleration) of subject 12.

Although sensors 20 are illustrated as two separate sensors disposed adjacent to pressure generator 14, this is not intended to be limiting. The sensors may include one or more sensors disposed in single location or a plurality of locations, such as for example, within pressure generator 14, within (or in communication with) conduit 28, within (or in communication with) interface appliance 30, and/or other locations.

In some implementations, one or more of sensors 20 may be placed outside of system 10 and nearer to subject 12. In such implementations, the output signals generated by the externally located sensors 20 can be relayed to processor 24 by wired and/or wireless configuration. An independent user interface may be included with the externally located sensors 20 that receives the output signals generated by sensors 20, processes the output signals implementing some or all of the techniques described herein, and/or displaying at least some of the determined information.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination.

Generally, processor 24 is configured to determine the respiratory state of subject 12. Processor 24 is further configured to control pressure generator 14 in generation of the pressurized flow of breathable gas such that one or more parameters of the pressurized flow of breathable gas vary in accordance with a therapy regimen that defines the one or more parameters as a function of respiratory state. To detect respiratory state, processor 24 may be configured to identify transitions in respiratory state based on the shape of flow (and/or other fluid parameters) of the pressurized flow of breathable gas. The identification of transitions in respiratory state may be independent from sensing and/or estimating fluid parameters at or near the airway of subject 12 (e.g., at interface appliance 30). As such, it may not require accurate leak and/or loss estimation. In some implementations, processor 24 may be configured to identify transitions in respiratory state based on changes in the first time derivative of flow.

As is shown in FIG. 1, processor 24 may be configured to execute one or more computer program modules. The one or more computer program modules may include one or more of a fluid parameter module 32, a control module 34, a volume determination module 36, an inspiration pressure module 37, a spontaneous respiration module 38, an arousal detection module 40, a rate determination module 42, a boost determination module 44, an expiration pressure module 46, and/or other modules. Processor 24 may be configured to execute modules 32, 34, 36, 37, 38, 40, 42, 44, and/or 46 by software; hardware; firmware; some combination of software, hardware, and/or firmware; and/or other mechanisms for configuring processing capabilities on processor 24.

It should be appreciated that although modules 32, 34, 36, 37, 38, 40, 42, 44, and 46 are illustrated in FIG. 1 as being co-located within a single processing unit, in implementations in which processor 24 includes multiple processing units, one or more of modules 32, 34, 36, 37, 38, 40, 42, 44, and/or 46 may be located remotely from the other modules. The description of the functionality provided by the different modules 32, 34, 36, 37, 38, 40, 42, 44, and/or 46 described below is for illustrative purposes, and is not intended to be limiting, as any of modules 32, 34, 36, 37, 38, 40, 42, 44, and/or 46 may provide more or less functionality than is described. For example, one or more of modules 32, 34, 36, 37, 38, 40, 42, 44, and/or 46 may be eliminated, and some or all of its functionality may be provided by other ones of modules 32, 34, 36, 37, 38, 40, 42, 44, and/or 46. As another example, processor 24 may be configured to execute one or more additional modules that may perform some or all of the functionality attributed below to one of modules 32, 34, 36, 37, 38, 40, 42, 44, and/or 46.

The fluid parameter module 32 is configured to determine one or more fluid parameters of the pressurized flow of breathable gas. The fluid parameter module 32 determines the one or more fluid parameters of the pressurized flow of breathable gas based on the output signals generated by sensors 20. The one or more fluid parameters determined by breathing parameter module 32 may include a flow, a volume, a pressure, a composition (e.g., concentration(s) of one or more constituents), humidity, temperature, acceleration, velocity, acoustics, changes in a parameter indicative of respiration, and/or other fluid parameters.

Control module 34 is configured to control pressure generator 14 to adjust the parameters of the pressurized flow of breathable gas in accordance with a therapy regimen. The therapy regimen provides the pressurized flow of breathable gas to the airway of subject 12 such that the average tidal volume of breaths subject 12 is maintained, the respiratory rate of the subject may be maintained, and/or the positive end expiratory pressure of the subject may be maintained. The therapy regimen may include and/or be related to AVAPS, ACV, and/or other volume therapies. This type of therapy is different from pressure support therapies, such as Positive Airway Pressure ("PAP") therapies, in which the airway of subject 12 is supported, but tidal volume and/or respiratory rate are not maintained. Instead, PAP therapies typically only control pressure to maintain the structural competence of the airway at prescribed levels without regard for the tidal volume and/or the respiratory rate.

The therapy regimen provided by control module 34 is a bi-level therapy. In this therapy regimen, the level of pressure of the pressurized flow of breathable gas during exhalation is maintained at an expiratory level (known as Expiratory Positive Airway Pressure or EPAP). During inspirations, the pressure level of the pressurized flow of breathable gas is increased to ensure subject 12 will take in enough gas to maintain the average tidal volume. Changes between Inspiration Positive Airway Pressure ("IPAP") and EPAP are triggered in accordance with a respiratory rate. Breaths taken in accordance with the respiratory rate include spontaneous breaths (e.g., breaths in which subject 12 is spontaneously taking gas into the lungs during inspiration and/or spontaneously exhausting gas from the lungs during expiration) and non-spontaneous breaths (e.g., breaths in which the movement of gas is due entirely (or substantially so) to changes in the level of the pressure of the pressurized flow of breathable gas).

Volume determination module 36 is configured to monitor the tidal volume of breaths during the delivery of the pressurized flow of breathable gas to subject 12. This may include determining the tidal volumes of individual breaths, determining an average tidal volume over a number of breaths, determining an average tidal volume over a sliding window of time, and/or determining other tidal volumes. The determination(s) of tidal volume may be made based on one or more fluid parameters determined by fluid parameter module 32 and/or the output signal(s) output by sensors 20.

Inspiration pressure module 37 is configured to determine a baseline level of IPAP. The inspiration pressure module is configured to determine the baseline level of IPAP so that the average tidal volume of the respiration of subject 12 will be maintained at a target average tidal volume. The target average tidal volume may be determined based on input to system 10 from subject 12, a caregiver, a therapy decision-maker, a researcher, and/or other users. In one embodiment, changes to the baseline level of IPAP are restricted by a maximum rate of change. The maximum rate of change may be greater than or equal to about 3 cm H2O/minute. This may be faster than conventional AVAPS and/or ACV therapy systems. This more dynamic control over the baseline level of IPAP may enhance the comfort of subject 12 by adjusting more quickly to changes in respiration caused by subject 12 shifting his body position.

Spontaneous respiration module 38 is configured to identify spontaneous breaths taken by subject 12. The identification of spontaneous breaths is based on the output signal(s) generated by sensors 20. In one embodiment, such identification is based on one or more fluid parameters determined by fluid parameter module 32 from the output signal(s) generated by sensors 20.

Arousal detection module 40 is configured to detect arousals of subject 12 during a therapy session. In one embodiment, arousals of subject 12 are determined based on identifications of spontaneous breaths by spontaneous respiration module 38. During sleep, subject 12 will tend to have fewer spontaneous breaths. Thus, arousal detection module 40 may detect an arousal based on an increase in spontaneous breaths. An increase in spontaneous breaths may be identified by comparing a rate at which spontaneous breaths occur with a threshold level, comparing an amount of spontaneous breaths during a sliding window in time with a threshold amount, and/or identified by another technique. In one embodiment, sensors 20 include one or more sensors conveying information about movement of subject 12. The arousal detection module 40 may be configured to detect arousals based on movement of subject 12 indicated by user interface 20. Other mechanisms for detecting arousals are contemplated.

Rate determination module 42 is configured to determine the therapeutic respiratory rate used to trigger transitions between IPAP and EPAP. In conventional AVAPS and/or ACV therapy systems, the respiratory rate may be determined based primarily or solely on a rate that is input by subject 12, a caregiver, a therapy decision-maker, a researcher, and/or other users. By contrast, rate determination module 42 is configured to determine the respiratory rate based on spontaneous respiration by subject 12. The rate determination module 42 assesses the respiratory rate of subject 12 early in a therapy session (e.g., at the beginning of a night) and maintains the respiratory rate appropriately throughout the therapy session. By dynamically determining the respiratory rate controlling tidal volume (e.g., with the IPAP level determined by inspiration pressure module 39), the subject's 12 minute ventilation may be indirectly sustained.

At the end of expiration, there is a highly variable time period that may last as long as one complete breath cycle when near zero flow is observed in the airway of subject 12 and the lungs remain at a constant volume. This period, sometimes referred to as expiratory pause, has been researched by both psychologists and physicians. It acts as a rest period for the muscles in the respiratory system, prevents the build up of excess oxygen and also allows arterial blood pressure stabilization while the left ventricle fills. With the support of mechanical ventilation provided by system 10 reducing the work of breathing for subject 12, extended rest periods are not necessary. Furthermore, when the normal unassisted gas exchange rate of the subject 12 is insufficient to properly reduce $CO_2$ levels in the blood stream, there may be some benefit to pace the respiratory rate during sleep by shortening the end expiratory pause. In essence, system 10 is programmed to lead the chemoreceptive mechanism in the hypercapnic subject 12 by initiating a breath prior to the central nervous system.

In one embodiment, the algorithm implemented by rate determination module 42 to determine the therapeutic respiratory rate implements the early and fastest spontaneous respiratory rate of subject 12 as a seed. A rolling window of spontaneous breath times is maintained in memory (e.g., electronic storage 16). The window may include between 12 to 50 breaths. In one embodiment, the window includes about 30 breaths. A breath time is entered into the window if it qualifies. A breath is considered by rate determination module 42 to "qualify" if (1) it began and ended with a patient effort that spontaneously triggered the device from the expiratory to inspiratory phase; and (2) the delivered tidal volume during the breath was near a typical tidal volume (e.g., within a predetermined amount). The second qualifying factor prevents rapid shallow recovery breaths from artificially setting the therapeutic respiratory rate too high. The typical tidal volume (rather than the set average volume) is used to allow for the case when the max or min IPAP pressure setting is not suitable for the volume setting. This qualifying requirement also allows the determination and delivery of the appropriate IPAP level to take precedent over the auto-backup algorithm.

Rate determination module 42 is configured to determine a current average spontaneous breath time from the breath times in the stored window. A wakeful breath time is set equal to the current average spontaneous breath time (A) if the current average spontaneous breath time is at or above a minimum (e.g., predetermined, user configurable, determined at manufacture, determined dynamically, and/or a minimum that is otherwise determined), and (B) if at least a threshold percentage of the breaths are spontaneous. The threshold percentage may be a static percentage, or may change over the course of a therapy session. For example, at the beginning of the therapy session, the threshold percentage may be relatively high value (e.g., 100%), as subject 12 should be awake and relatively alert. As the therapy session proceed (and/or the wakefulness and/or attentiveness of subject 12 wanes), the threshold percentage may be reduced to a lower value, such as about 70%, for example. The reduction in the threshold percentage may include a graduate reduction, a sloping reduction, a switch from the high value to the low value, and/or other techniques for reducing a value.

Rate determination module 42 is configured to set a therapeutic breath time based on the wakeful breath time. In one embodiment, the therapeutic breath time is set by rate determination module 42 to the lesser of 1.14 times the wakeful breath rate or 2 breaths per minute less than the wakeful breath time. This embodiment for determining the therapeutic breath time is illustrated by the following relationship:

$$TBT = \text{lesser\_of}\left(1.14 \cdot WBT, \frac{60}{\left(\frac{60}{WBT}\right) - 2}\right); \quad (1)$$

where TBT represents the therapeutic breath time, and WBT represents the wakeful breath time.

For a given breath, the total respiration time is the sum of inspiratory time (e.g., the therapeutic breath time) and an expiratory time. This can be represented as:

$$TRT = TBT + ET; \quad (2)$$

where TRT represents therapeutic respiratory time; and ET represents expiratory time. The therapeutic respiratory rate is the inverse of the therapeutic respiratory time.

In one embodiment, the rate determination module 42 is configured to determine the expiratory time dynamically. For example, rate determination module 42 may determine the expiratory time according to the following relationship:

$$ET = VT \cdot (1 - m); \quad (3)$$

where VT is a variable time, and m is the proportion (i.e., from 0 to 1) of non-spontaneous breaths over a sliding window of past breaths. In one embodiment, this sliding window of past breaths is about 12. Rate determination module 42 is configured to determine the variable time proportional to the therapeutic breath time. For example, rate determination module 42 may determine the variable time as:

$$VT = 0.12 \cdot TBT. \quad (4)$$

It will be appreciated that if the sliding window of past breaths used to determine m is 12, when subject 12 enters a sleepful state and reduces his respiratory rate, system 10 will increase his respiratory rate up to approximately 90% of the wakeful breath rate in as little as 12 breaths. The variable time adjusts the therapeutic respiratory rate from approximately 75% to 90% of the patient's rate while he was awake based on the number of non-spontaneous breaths. This provides a number of comfort features for subject 12 including a smooth transition as subject 12 falls asleep and system 10 begins to control the respiratory rate, and allowing subject 12 to spontaneously breathe after an arousal from deep sleep.

During a therapy session, after subject 12 has gone to sleep, as subject 12 experiences an arousal, the therapeutic respiratory rate may feel artificially high to subject 12. This may cause discomfort to subject 12, and may result in subject 12 being awakened fully and/or having trouble going back to sleep. To avoid this discomfort, and/or for other reasons, in addition to and/or in place of the adjustments to the variable m discussed above, rate determination module 42 may be configured to reduce the therapeutic respiratory rate during arousals. This involves reducing the therapeutic respiratory rate (e.g., by a specified amount, by a predetermined amount, in a graduated manner, and/or otherwise reducing the rate) during detection of an arousal by arousal detection module 40.

In controlling pressure generator 14 to transition the pressure level of the pressurized flow of breathable gas between the IPAP and the EPAP, control module 34 is configured to rely on spontaneous respiration module 38 and rate determination module 42. For example, at the end of a breath (e.g., during expiration) control module 34 is configured to trigger pressure generator 14 to adjust the level of pressure from EPAP to IPAP responsive to either spontaneous respiration module 38 detecting a spontaneous inspiration, or passage of an amount of time from a respiratory event (e.g., from initiation of the previous inspiration, from end of the previous inspiration, and/or other times) corresponding to the therapeutic respiratory rate without detection of a spontaneous inspiration. Responsive to either of these phenomena, control module 34 controls pressure generator 14 to increase the level of pressure from IPAP to EPAP.

Control module 34 is further configured to modify pressure responsive to spontaneous breathing. This includes modifying pressure during a non-spontaneous breath that has been triggered in accordance with the therapeutic respiratory rate. Responsive to identification by spontaneous respiration module 38 of spontaneous breathing against the non-spontaneous breath, control module 34 is configured to control pressure generator 14 to modify pressure to support the spontaneous breath, rather than continuing with the non-spontaneous breath. By way of non-limiting example, responsive to spontaneous respiration module 38 detecting spontaneous expiratory effort during inspiration of a non-spontaneous breath, control module 34 may be configured to control pressure generator 14 to switch from IPAP to EPAP even though the inspiration of the non-spontaneous breath has not been completed. This may enhance the comfort of system 10 to subject 12, as subject 12 does not have to exhale through the elevated pressure of IPAP.

Because during a spontaneous inspiration, movement of gas into the lungs is aided by the respiratory effort of subject 12 along with the pressure of the pressurized flow of breathable gas. By contrast, during a non-spontaneous inspiration, movement of gas into the lungs is accomplished solely or primarily by virtue of the pressure of the pressurized flow of breathable gas. To accommodate this difference, control module 34 may be configured to control pressure generator 14 such that IPAP for spontaneous breaths (as identified by spontaneous respiration module 38) is different than IPAP for non-spontaneous breaths (breaths triggered by the therapeutic respiratory rate). By way of non-limiting example, in one embodiment, control module 34 controls pressure generator 14 such that responsive to a given breath being a spontaneous breath, IPAP is provided at a baseline level. Responsive to the given breath being a non-spontaneous breath, IPAP is provided at a boosted level that is higher than the baseline level. The higher boosted level will help to maintain the average tidal volume in the absence of the respiratory effort of subject 12.

Figure 2:
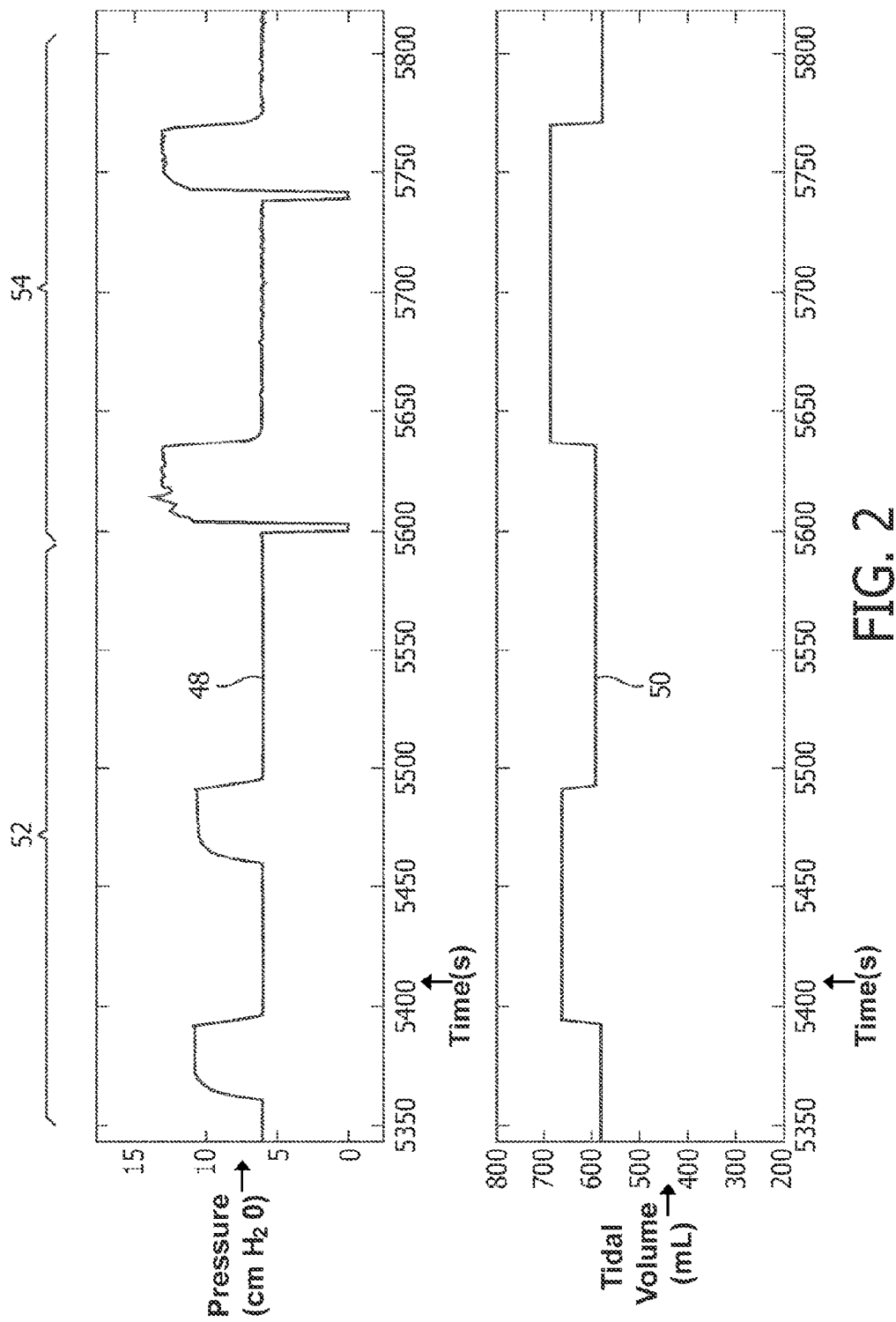
FIG. 2 illustrates two plots taken over spontaneous and non-spontaneous breaths by a subject.

By way of illustration, FIG. 2 includes two plots that depict the implementation of a baseline level of IPAP and a boosted level of IPAP. In particular, FIG. 2 includes a pressure plot 48 and a tidal volume plot 50. Pressure plot 48 shows pressure as a function of time for two spontaneous breaths 52 and two non-spontaneous breaths 54. Tidal volume plot 50 shows tidal volume as a function of time for the spontaneous breaths 52 and the non-spontaneous breaths 54. As can be seen in pressure plot 48, the IPAP for non-spontaneous breaths 54 is about 3 cm H2O higher than the IPAP for spontaneous breaths 52. Nevertheless, as is shown in tidal volume plot 50, the tidal volume remains stable between spontaneous breaths 52 and non-spontaneous breaths 54 at about 600 mL.

Returning to FIG. 1, in one embodiment, the boosted level of IPAP is set at the sum of the baseline level of IPAP and a boost amount of pressure. The boost determination module 44 is configured to determine the boost amount of pressure for subject 12. The boost determination module 44 may be configured such that the determination of the boost amount is based on respiration of subject 12, based on input to system 10 by a user, and/or based on other criteria. For example, the boost amount may be based on the output signal(s) generated by sensors 20, and/or other metrics of the respiration of subject 12.

Figure 3:
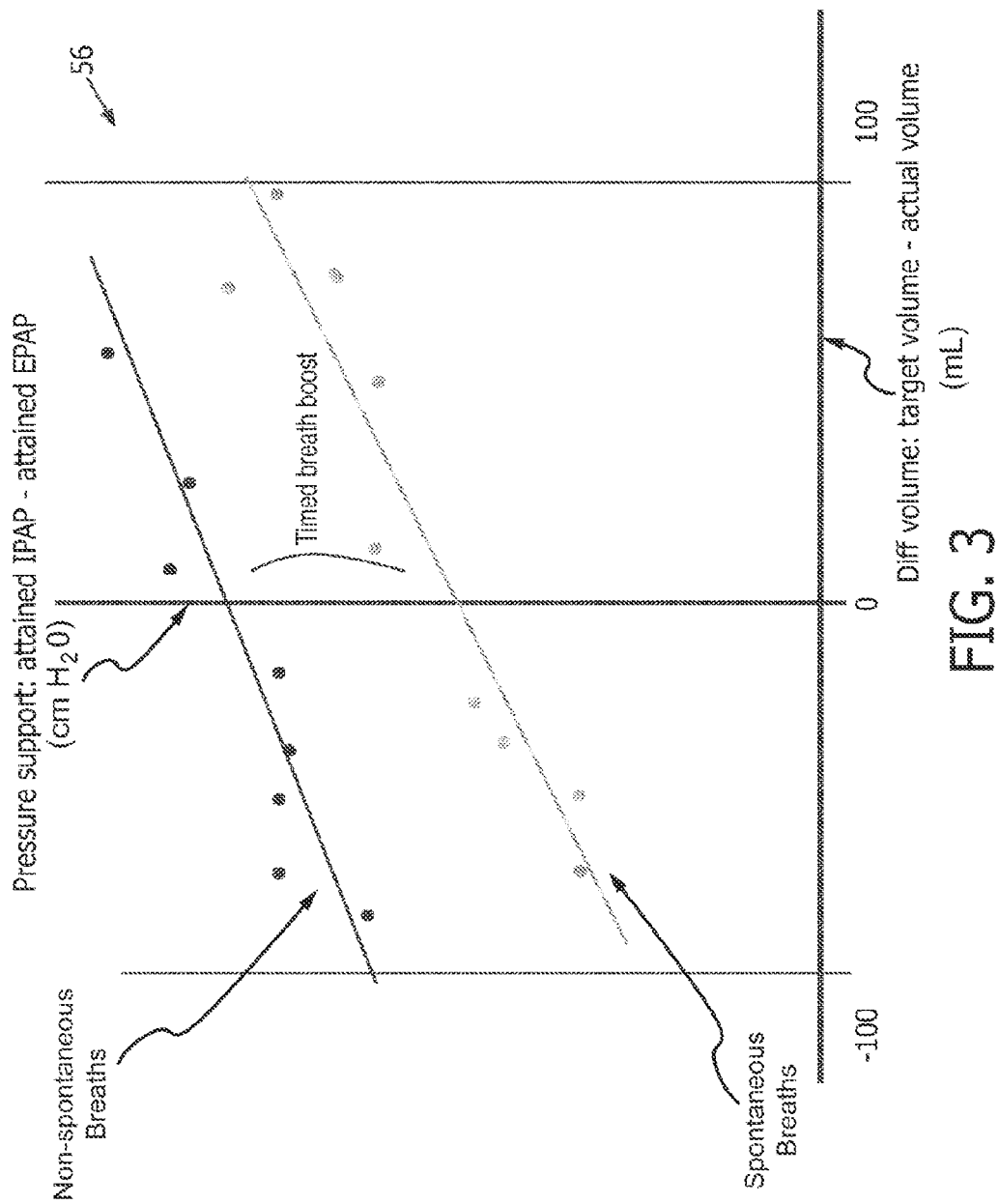
FIG. 3 illustrates a plot used to determine a boost amount of pressure.

By way of illustration, FIG. 3 depicts one potential technique for determining the boost amount. FIG. 3 shows a plot 56 of points corresponding to individual breaths. The metrics plotted for each of the individual breaths is the difference between IPAP and EPAP for a breath versus the difference between the target tidal volume and the actual tidal volume of the breath. Two lines are fitted to the points, one for points corresponding to spontaneous breaths and one for points corresponding to non-spontaneous breaths. The difference along the y-axis for these two lines is implemented as the boost amount. The difference along the y-axis may be determined as the average difference along the y-axis, the difference of the y-intercepts, and/or other differences.

Returning to FIG. 1, control module 34 is configured to implement the boost amount determined by boost determination module 44 and the baseline level for IPAP determined by inspiration pressure module 37 to determine the boosted level for IPAP. The expiration pressure module 46 is configured to determine the appropriate EPAP pressure level. The determination of the EPAP pressure level by expiration pressure module 46 may be ongoing and/or dynamic during a therapy session. In one embodiment, expiration pressure module 46 is configured to implement the technique for determining EPAP described in U.S. Pat. No. 7,267,122, which is hereby incorporated by reference into this disclosure in its entirety. This is not intended to be limiting, as the expiration pressure module 46 may implement any technique for determining the EPAP pressure level that will maintain a positive end expiratory pressure for subject 12. The positive end expiratory pressure level may be determined dynamically and/or be a fixed value.

Maintenance of the positive end expiratory pressure level may maintain the structural integrity of the airway at the end of expiration to reduce apneas and/or airway occlusions. Similarly, maintenance of the positive end expiratory pressure level may reduce the effort required of subject 12 to initiate a next spontaneous breath. As such, determination of an appropriate EPAP level by expiration pressure module 46 may enhance comfort, increase spontaneous breathing, enhance airway integrity, and/or enhance other aspects of the therapy.

Figure 4:
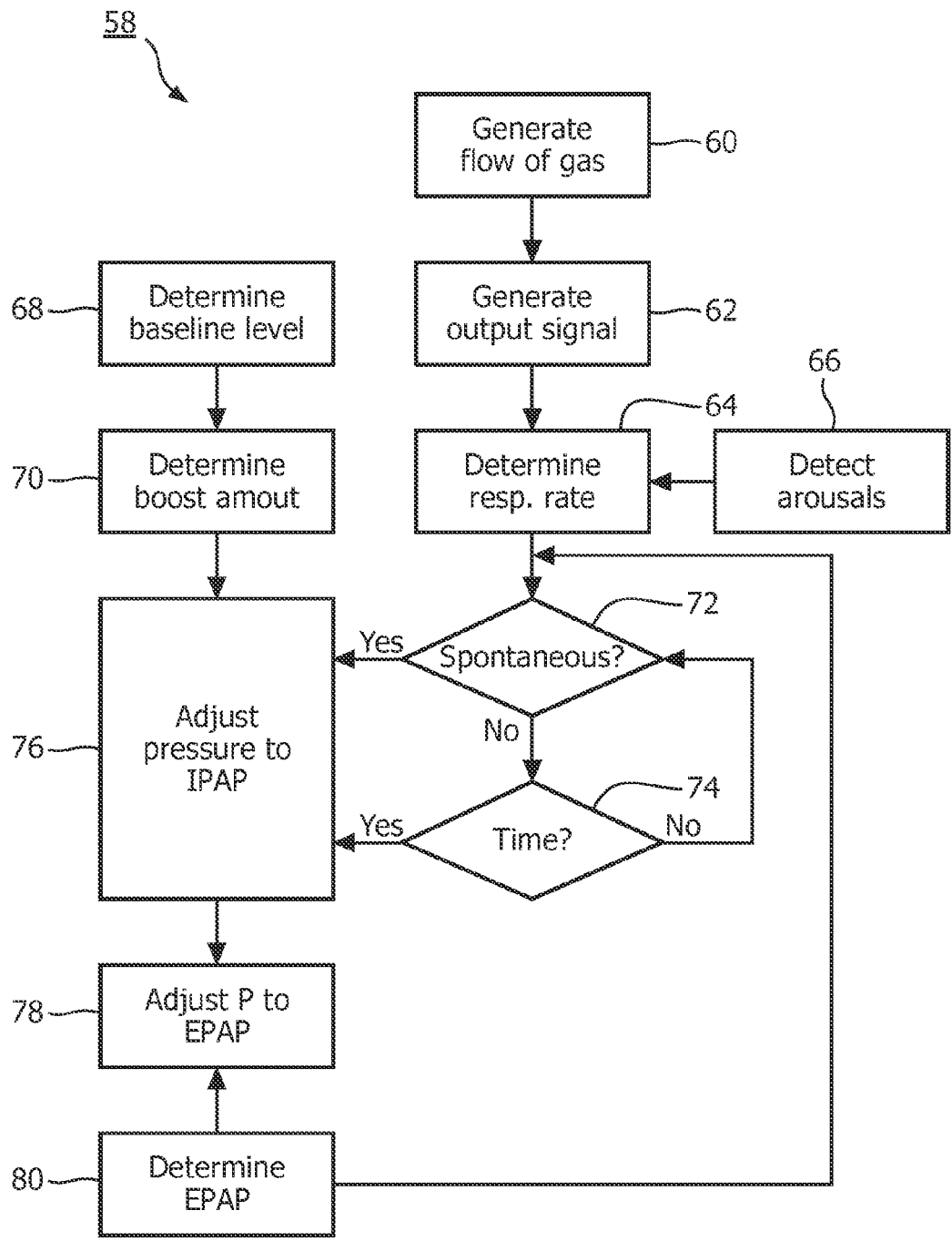
FIG. 4 illustrates a method of delivering a pressurized flow of breathable gas to the airway of a subject.

FIG. 4 illustrates a method 58 of delivering a pressurized flow of breathable gas to the airway of a subject. The operations of method 58 presented below are intended to be illustrative. In some embodiments, method 58 may be accomplished with one or more additional operations not described, and/or without one or more of the operations discussed. Additionally, the order in which the operations of method 58 are illustrated in FIG. 4 and described below is not intended to be limiting.

In some embodiments, some or all of the operations of method 58 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 58 in response to instructions stored electronically on an electronic storage medium. The one or more processing devices may include one or more devices configured through hardware, firmware, and/or software to be specifically designed for execution of one or more of the operations of method 58.

At an operation 60, a pressurized flow of breathable gas is generated for delivery to the airway of the subject. In one embodiment, operation 60 is performed by a pressure generator similar to or the same as pressure generator 14 (shown in FIG. 1 and described above) under the control of a control module similar to or the same as control module 34 (shown in FIG. 1 and described above).

At an operation 62, one or more output signals are generated by one or more sensors. The one or more output signals convey information related to respiratory effort by the subject, one or more fluid parameters of the pressurized flow of breathable gas, one or more breathing parameters of subject 12, and/or other information. In one embodiment, operation 62 is performed by one or more sensors similar to or the same as sensors 20 (shown in FIG. 1 and described above).

At an operation 64, a therapeutic respiratory rate is determined. The therapeutic respiratory rate may be determined based on spontaneous respiration by the subject at or near commencement of a therapy session. Determination of the respiratory rate may be ongoing during the therapy session and may be adjusted to accommodate, for example, arousals of the subject. Arousals may be detected at an operation 66. Responsive to detection of an arousal at operation 66, the respiratory rate may be reduced for the duration of the arousal. In one embodiment, operation 64 is performed by a rate determination module similar to or the same as rate determination module 42 (shown in FIG. 1 and described above). In one embodiment, operation 66 is performed by an arousal detection module similar to or the same as arousal detection module 40 (shown in FIG. 1 and described above).

At an operation 68, a baseline pressure level for IPAP is determined. The determination of the baseline level may be based on a target tidal volume for the therapy session. The baseline pressure level may be determined to ensure that the target tidal volume is maintained during spontaneous breaths by the subject. In one embodiment, operation 68 is performed by an inspiration pressure module similar to or the same as inspiration pressure module 37 (shown in FIG. 1 and described above).

At an operation 70, a boost amount of pressure is determined. The boost amount of pressure is the amount of pressure to be added to the baseline level for IPAP during non-spontaneous breaths. In one embodiment, operation 70 is performed by a boost determination module similar to or the same as boost determination module 44 (shown in FIG. 1 and described above).

At an operation 72, a determination is made as to whether the subject has initiated a spontaneous breath. In one embodiment, operation 72 is performed by a spontaneous respiration module similar to or the same as spontaneous respiration module 38 (shown in FIG. 1 and described above). Responsive to a determination that the subject has not initiated a spontaneous breath, method 58 proceeds to an operation 74.

At operation 74, a determination is made as to whether a non-spontaneous breath should be initiated. This determination is made based on a time of a previous breathing event (e.g., initiation of a previous breath, initiation of a previous expiration, end of a previous inspiration, and/or other breathing events) and the therapeutic respiratory rate to ensure that the therapeutic respiratory rate is maintained. Responsive to a determination that a non-spontaneous breath should not be initiated, method 58 returns to operation 72. In one embodiment, operation 74 is performed by a control module similar to or the same as control module 34 (shown in FIG. 1 and described above).

Responsive to a determination at operation 72 that a spontaneous breath has been initiated or responsive to a determination at operation 74 that a non-spontaneous breath should be initiated, method 58 passes to an operation 76. At operation 76, the pressure level of the pressurized flow of breathable gas is maintained at an IPAP pressure level. Responsive to a determination at operation 72 that a spontaneous breath has been initiated, the IPAP pressure level at operation 76 is set at the baseline level determined at operation 68. Responsive to a determination at operation 74 that a non-spontaneous breath should be initiated, the IPAP pressure level at operation 76 is set at a boosted level that is higher than the baseline level. The boosted level may be the sum of the baseline level and the boosted pressure amount. At operation 76, the delivery of the pressurized flow of breathable gas at the IPAP pressure level may be disrupted responsive to a detection of spontaneous expiration by the subject. In one embodiment, operation 76 is performed by pressure generator similar to or the same as pressure generator 14 (shown in FIG. 1 and described above) under the control of a control module similar to or the same as control module 34 (shown in FIG. 1 and described above).

At an operation 78, the pressure of the pressurized flow of breathable gas is adjusted to an EPAP level for expiration by the subject. In one embodiment, operation 78 is performed by pressure generator similar to or the same as pressure generator 14 (shown in FIG. 1 and described above) under the control of a control module similar to or the same as control module 34 (shown in FIG. 1 and described above).

At an operation 80, the EPAP level for the pressurized flow of breathable gas is determined. In one embodiment, operation 80 is performed by an expiration pressure module similar to or the same as expiration pressure module 46 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to deliver a pressurized flow of breathable gas to an airway of a subject, the system comprising:
   a pressure generator configured to generate a pressurized flow of breathable gas for delivery to the airway of the subject;
   one or more sensors configured to generate output signals conveying information related to respiratory effort by the subject; and
   one or more hardware processors configured by machine-readable instructions to control the pressure generator in accordance with a therapy regimen, wherein controlling the pressure generator in accordance with the therapy regimen comprises:
      determining an inspiratory pressure level that maintains a target average tidal volume and causing the pressure generator to generate the pressurized flow of breathable gas at the determined inspiratory pressure level during inspiration of the subject;
      determining a current respiratory rate of the subject during wakefulness based on the generated output signals;
      determining a therapeutic respiratory rate for sleep based on the current respiratory rate, the therapeutic respiratory rate being slower than the current respiratory rate;
      controlling the pressure generator to slow the current respiratory rate to reduce a difference between the current respiratory rate and the therapeutic respiratory rate;
      determining an expiratory pressure level that maintains a positive end expiratory pressure in the airway of the subject and causing the pressure generator to generate the pressurized flow of breathable gas at the determined expiratory pressure level during expiration of the subject;
      identifying, based on the generated output signals, spontaneous breaths taken by the subject; and
      responsive to a given breath not being identified as being a spontaneous breath, maintaining the pressure of the pressurized flow of breathable gas during inspiration of the given breath at a boosted level, wherein the boosted level is determined based on:
         plotted data points corresponding to a difference between the determined inspiratory pressure level and the determined expiratory pressure level versus a difference between target tidal volume and actual tidal volume for spontaneous breaths;
         plotted data points corresponding to the difference between the determined inspiratory pressure level and the determined expiratory pressure level versus the difference between target tidal volume and actual tidal volume for non-spontaneous breaths;
         a first line fitted to the data points corresponding to the spontaneous breaths,
         a second line fitted to the data points corresponding to the non-spontaneous breaths; and
         a difference determined between the first line and the second line at a given difference between target tidal volume and actual tidal volume.

2. The system of claim 1, wherein the determined inspiratory pressure level is an inspiratory baseline pressure level and wherein:
   responsive to the given breath being identified as being a spontaneous breath, the pressure of the pressurized flow of breathable gas during inspiration of the given breath is maintained at the baseline level.

3. The system of claim 1, wherein the one or more hardware processors are further configured to determine the therapeutic respiratory rate based on spontaneous breathing of the subject during wakefulness monitored at or near commencement of a therapy session in which the pressure generator is controlled to generate the pressurized flow of breathable gas in accordance with the therapy regime.

4. The system of claim 3, wherein the one or more hardware processors are further configured to detect arousals of the subject during the therapy session and cause the pressure generator to reduce the therapeutic respiratory rate during detected arousals.

5. The system of claim 1, wherein the determined inspiratory pressure level is an inspiratory baseline pressure level and wherein the boosted level of pressure is equal to the sum of the baseline level and the determined difference between the first line and the second line.

6. The system of claim 1, wherein the one or more hardware processors are configured such that the determined current respiratory rate of the subject is a spontaneous respiratory rate of the subject.

7. The system of claim 3, wherein the one or more hardware processors are configured to determine the therapeutic respiratory rate based on the spontaneous breathing of the subject responsive to a threshold percentage of the breaths of the subject at or near commencement of the therapy session being spontaneous.

8. A method for delivering a pressurized flow of breathable gas to an airway of a subject with a delivery system, the delivery system comprising a pressure generator, one or more sensors, and one or more hardware processors, the method comprising:
   generating, with the pressure generator, the pressurized flow of breathable gas for delivery to the airway of the subject;
   generating, with the one or more sensors, output signals conveying information related to respiratory effort by the subject;
   determining, with the one or more hardware processors, an inspiratory pressure level that maintains a target average tidal volume and causing the pressure generator to generate the pressurized flow of breathable gas at the determined inspiratory pressure level during inspiration of the subject;
   determining, with the one or more hardware processors, an expiratory pressure level that maintains a positive end expiratory pressure in the airway of the subject and causing the pressure generator to generate the pressurized flow of breathable gas at the determined expiratory pressure level during expiration of the subject;
   determining a current respiratory rate of the subject during wakefulness based on generated output signals;
   determining a therapeutic respiratory rate for sleep based on the current respiratory rate, the therapeutic respiratory rate being slower than the current respiratory rate,
   controlling the pressure generator to generate the pressurized flow of breathable gas in accordance with a therapy regimen to slow the current respiratory rate to reduce a difference between the current respiratory rate and the therapeutic respiratory rate;
   identifying, based on the generated output signals, spontaneous breaths taken by the subject; and
   responsive to a given breath not being identified as being a spontaneous breath, maintaining the pressure of the pressurized flow of breathable gas during inspiration of the given breath at a boosted level, wherein the boosted level is determined based on:
plotted data points corresponding to a difference between the determined inspiratory pressure level and the determined expiratory pressure level versus a difference between target tidal volume and actual tidal volume for spontaneous breaths;
plotted data points corresponding to the difference between the determined inspiratory pressure level and the determined expiratory pressure level versus the difference between target tidal volume and actual tidal volume for non-spontaneous breaths;
a first line fitted to the data points corresponding to the spontaneous breaths,
a second line fitted to the data points corresponding to the non-spontaneous breaths; and
a difference determined between the first line and the second line at a given difference between target tidal volume and actual tidal volume.

9. The method of claim 8, wherein the determined inspiratory pressure level is an inspiratory baseline pressure level and wherein controlling the pressure generator to generate the pressurized flow of breathable gas further comprises:
responsive to the given breath being identified as being a spontaneous breath, maintaining the pressure of the pressurized flow of breathable gas during inspiration of the given breath at a baseline level.

10. The method of claim 8, wherein determination of the therapeutic respiratory rate is based on spontaneous breathing of the subject during wakefulness monitored at or near commencement of a therapy session in which the generation of the pressurized flow of breathable gas is controlled in accordance with the therapy regime.

11. The method of claim 10, further comprising:
detecting arousals of the subject during the therapy session; and
controlling the pressure generator to reduce the therapeutic respiratory rate during detected arousals.

12. The method of claim 8, wherein the determined inspiratory pressure level is an inspiratory baseline pressure level and wherein the boosted level of pressure is equal to the sum of the baseline level and the determined difference between the first line and the second line.

13. The method of claim 8, wherein the determined current respiratory rate of the subject is a spontaneous respiratory rate of the subject.

14. The method of claim 10, wherein the therapeutic respiratory rate is determined based on the spontaneous breathing of the subject responsive to a threshold percentage of the breaths of the subject at or near commencement of the therapy session being spontaneous.

15. A system configured to deliver a pressurized flow of breathable gas to an airway of a subject, the system comprising:
means for generating a pressurized flow of breathable gas for delivery to the airway of the subject;
means for generating output signals conveying information related to respiratory effort by the subject;
means for determining an inspiratory pressure level that maintains a target average tidal volume and causing the means for generating the pressurized flow of breathable gas to generate the pressurized flow of breathable gas at the determined inspiratory pressure during inspiration of the subject;
means for determining an expiratory pressure level that maintains a positive end expiratory pressure in the airway of the subject and causing the means for generating the pressurized flow of breathable gas to generate the pressurized flow of breathable gas at the determined expiratory pressure level during expiration of the subject;
means for determining a current respiratory rate of the subject during wakefulness based on generated output signals;
means for determining a therapeutic respiratory rate for sleep based on the current respiratory rate, the therapeutic respiratory rate being slower than the current respiratory rate;
means for controlling the means for generating the pressurized flow of breathable gas to generate the pressurized flow of breathable gas in accordance with a therapy regimen to slow the current respiratory rate to reduce a difference between the current respiratory rate and the therapeutic respiratory rate;
means for identifying, based on the generated output signals, spontaneous breaths taken by the subject; and
responsive to a given breath not being identified as being a spontaneous breath, means for maintaining the pressure of the pressurized flow of breathable gas during inspiration of the given breath at a boosted level, wherein the boosted level is determined based on:
plotted data points corresponding to a difference between the determined inspiratory pressure level and the determined expiratory pressure level versus a difference between target tidal volume and actual tidal volume for spontaneous breaths;
plotted data points corresponding to the difference between the determined inspiratory pressure level and the determined expiratory pressure level versus the difference between target tidal volume and actual tidal volume for non-spontaneous breaths;
a first line fitted to the data points corresponding to the spontaneous breaths,
a second line fitted to the data points corresponding to the non-spontaneous breaths; and
a difference determined between the first line and the second line at a given difference between target tidal volume and actual tidal volume.

16. The system of claim 15, wherein the determined inspiratory pressure level is an inspiratory baseline pressure level and wherein the means for controlling the means for generating the pressurized flow of breathable gas is configured such that:
responsive to the given breath being identified as being a spontaneous breath, the pressure of the pressurized flow of breathable gas during inspiration of the given breath is maintained at a baseline level.

17. The system of claim 15, wherein determination of the therapeutic respiratory rate is made based on spontaneous breathing of the subject during wakefulness monitored at or near commencement of a therapy session in which the generation of the pressurized flow of breathable gas is controlled in accordance with the therapy regime.

18. The system of claim 17, further comprising:
means for detecting arousals of the subject during the therapy session; and
means for reducing the therapeutic respiratory rate during detected arousals.

19. The system of claim 15, wherein the determined inspiratory pressure level is an inspiratory baseline pressure level and wherein the boosted level of pressure is equal to the sum of the baseline level and the determined difference between the first line and the second line.

20. The system of claim 15, wherein the determined current respiratory rate of the subject is a spontaneous respiratory rate of the subject.

21. The system of claim 17, wherein the therapeutic respiratory rate is determined based on the spontaneous breathing of the subject responsive to a threshold percentage of the breaths of the subject at or near commencement of the therapy session being spontaneous.

* * * * *